(12) United States Patent
Hsu (10) Patent No.: US 7,625,473 B2
(45) Date of Patent: Dec. 1, 2009

(54) TEST STRIP WITH IDENTIFICATION FUNCTION AND TEST INSTRUMENT USING THE SAME

(75) Inventor: Tien-Tsai Hsu, Hsinchu (TW)

(73) Assignee: HMD Biomedical Inc, Hsinchu (TW)

( * ) Notice: Subject to any disclaimer, the term of this patent is extended or adjusted under 35 U.S.C. 154(b) by 0 days.

(21) Appl. No.: 12/196,727

(22) Filed: Aug. 22, 2008

(65) Prior Publication Data
US 2009/0101500 A1   Apr. 23, 2009

(30) Foreign Application Priority Data
Oct. 19, 2007   (TW)   ............... 96139142 A (51) Int. Cl.
*G01N 27/327*   (2006.01)
*G01N 21/00*   (2006.01)
(52) U.S. Cl. ............ 204/403.02; 204/400; 422/55
(58) Field of Classification Search .......... 204/403.01–403.15; 422/50, 52, 55–58
See application file for complete search history.

(56) References Cited

U.S. PATENT DOCUMENTS

| 4,714,874 A | * | 12/1987 | Morris et al. ............ 324/601 |
| 7,491,303 B2 | * | 2/2009 | Sakata et al. ............ 204/400 |
| 2005/0279647 A1 | * | 12/2005 | Beaty .................... 205/792 |
| 2007/0068806 A1 | * | 3/2007 | Yang et al. ........... 204/403.01 |
| 2007/0068808 A1 | * | 3/2007 | Lee ..................... 204/403.01 |

FOREIGN PATENT DOCUMENTS

TW   96100251   1/2007

* cited by examiner

Primary Examiner—Alex Noguerola
(74) Attorney, Agent, or Firm—Ming Chow; Sinorica, LLC (57) ABSTRACT

The present invention discloses a test strip with an identification function and a test instrument using the same. The test strip of the present invention comprises a substrate, a test area on the substrate and an identification area also on the substrate. The identification area has at least two identification electrodes, at least one resistor element connected in parallel with the identification electrodes, and an electrode area coupling the identification electrodes and the resistor element. Thereby, the present invention provides many sets of identification signals to differentiate customers, test strips and test instruments.

14 Claims, 9 Drawing Sheets

TEST STRIP WITH IDENTIFICATION FUNCTION AND TEST INSTRUMENT USING THE SAME

BACKGROUND OF THE INVENTION

1. Field of the Invention

The present invention relates to a test technology, particularly to a test strip with an identification function and a test instrument using the same.

2. Description of the Related Art

Owing to the development of test strips and test instruments of biotests, it makes possibilities of home care and point of care, such as tests of glucose, cholesterol, uric acid, drugs, immunology, etc., are no more necessarily undertaken in a clinic or hospital but can be undertaken in an arbitrary place or even performed by a patient at home. Therefore, test strips and test instruments not only convenience patients but also save a lot of medical expenditure.

Figure 1:
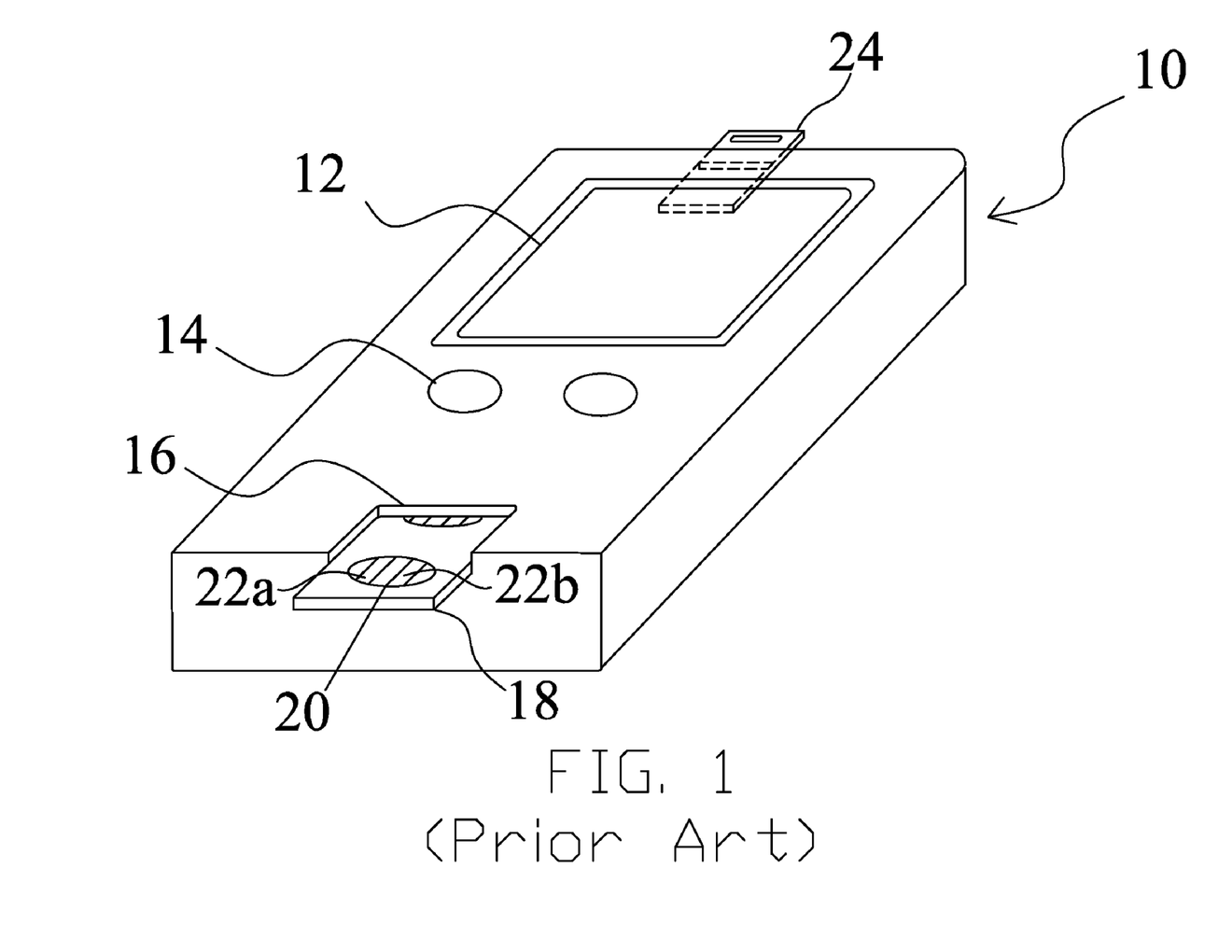
FIG. 1 is a perspective view schematically showing the structure of a conventional biotest instrument.
Figure 2:
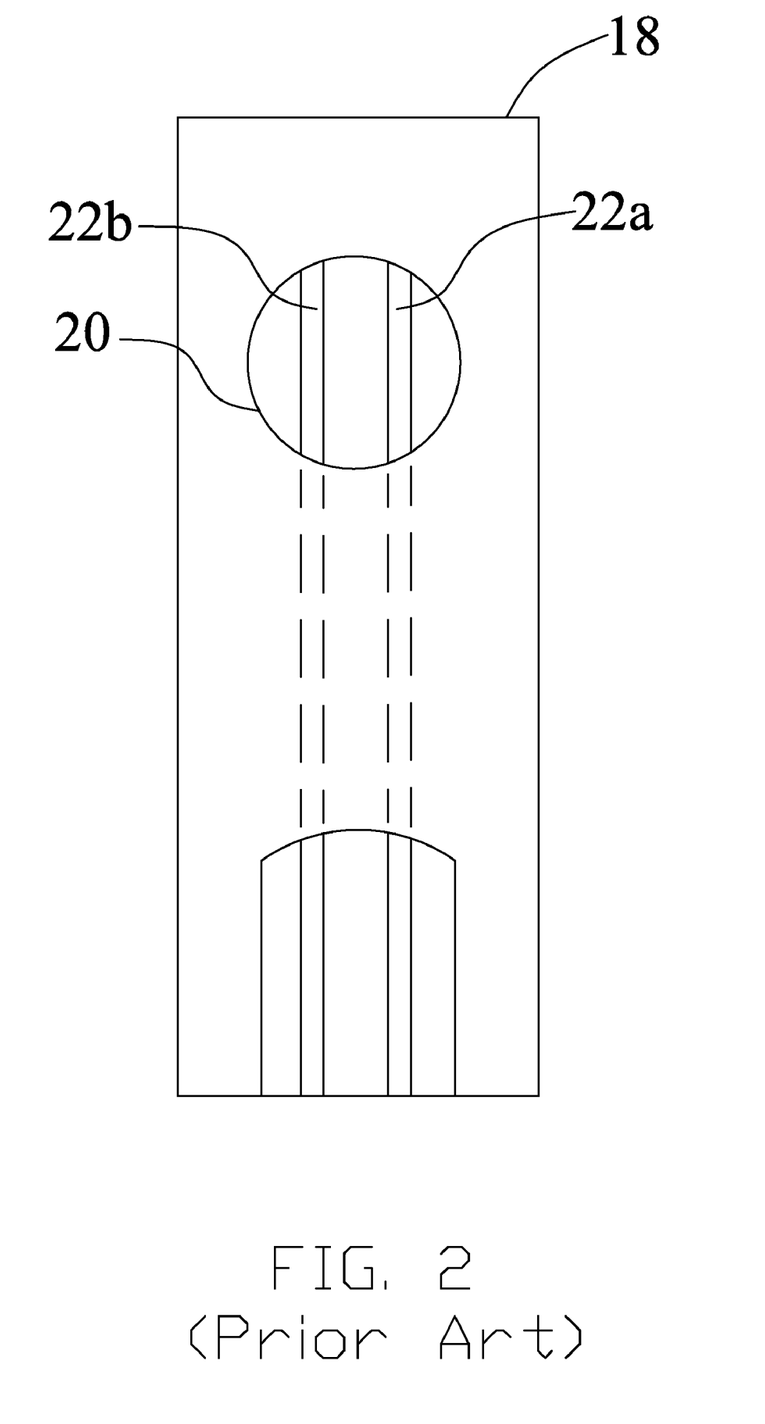
FIG. 2 is a diagram schematically showing the structure of a conventional electrochemical test strip.

Refer to FIG. 1. A U.S. Pat. No. 5,366,609 disclosed a biotest instrument 10 comprising a display unit 12, a button unit 14, an insertion slot 16 where an electrochemical test strip 18 is inserted, and a plug-in type code card 24 to be plugged in the biotest instrument 10. Refer to FIG. 2. The electrochemical test strip 18 has a test area 20 and a pair of electrodes 22a and 22b connected to the test area 20. The code card 24 contains the analysis parameters and operation procedures of the test strip 18. The biotest instrument 10 also comprises a controller and a sensor. The controller is coupled to the sensor, the display unit 12, the insert slot 14 and the code card 24. The sensor is coupled to the electrodes 22a and 22b. When the code card 24 is inserted into the biotest instrument 10, the controller reads the analysis parameters and operation procedures inside the code card 24 and controls the sensor to analyze the signal generated by the reaction of a tested liquid on the test area 20 and then outputs the test result to the display unit 12.

However, different batches of test strips need different code cards in the abovementioned prior art. A user has to keep watch for whether a correct code card is inserted into the test instrument. If a wrong code card is inserted, the test result will be incorrect. Therefore, the prior art is inconvenience for users and may give users incorrect information.

A US patent Publication No. 2007/0068806 disclosed an error-proof test strip, wherein the identification data is built in an identification electrode area of the test strip. The identification electrode area is coated with conductive materials with different impedances. After a test strip is inserted the test instrument, the test instrument can determine the specification of the test strip according to the impedances of the identification electrodes. In fabrication, the identification electrode areas of test strips are coated with different-impedance conductive materials to meet various test requirements, and the test instruments are programmed to meet the intended types of test strips. In this prior-art patent, each reaction electrode is cascaded to an identification electrode, and the test instrument needs an additional operational amplifier to implement measuring the impedances of the identification electrodes. Besides, the conductive materials providing the required impedances have to be determined before fabrication. Therefore, the identification electrode area of the prior art can only be used to differentiate the types of products and customers.

A US patent Publication No. 2007/0068808 disclosed a test strip, wherein a precise resistor is connected to an identification electrode and a reaction electrode via soldering, which increases the complexity and cost of fabrication. Further, the test instrument also needs an additional operational amplifier to implement measuring the impedances, which increases the structural complexity. Besides, the resistor providing the required impedances also has to be determined before fabrication. Therefore, the prior art is limited to only differentiating the types of products and customers.

A Taiwan patent application No. 96100251 disclosed a test strip, wherein the identification electrode area of the test strip has several identification electrodes, and a portion of the identification electrodes are fabricated into open circuit structures according to the required parameters or other conditions to provide different identification signals. However, the number of identification signals will be limited by the number of identification electrodes. When the number of identification electrodes is limited, the identification signals are unlikely to differentiate a lot of customers, many types of test strips, or many types of test instruments.

Therefore, it is necessary to provide a novel test strip and test instrument to overcome the problems in biotest technology.

SUMMARY OF THE INVENTION

One objective of the present invention is to provide a test strip with an identification function and a test instrument using the same to overcome the abovementioned conventional problems. The test strip of the present invention has an identification area containing identification electrodes and resistor elements, and the identification area generates digital and analog identification signals, whereby a test strip can incorporate analysis parameters, and whereby a user can fast obtain a correct test result without inserting a code card into a test instrument or inputting a test code or analysis parameters into a test instrument, and whereby the identification area of a test strip has sufficient identification signals to differentiate a lot of customers, many types of test strips, or many types of test instruments. Thus is overcome the problem of insufficient identification signals in the prior art.

The present invention proposes a test strip with an identification function, which comprises a substrate, a test area formed on the substrate and an identification area formed on the substrate. The identification area has N pieces of identification electrodes, at least one resistor element, and an electrode area. The N pieces of identification electrodes are used to generate digital identification signals, and $N \geq 2$. The resistor element is connected in parallel to the identification electrodes and used to generate analog identification signals. The electrode area is coupled to the identification electrodes and the resistor element. The resistor element may have m sets of resistance values, and $m \geq 1$. Thereby, the identification area can provides $m \times 2^N$ sets of identification signals. After receiving the identification signal, the test instrument obtains the test code, analysis parameters, expiry date, and/or batch number of the test strip to perform judgment and calibration.

Below, the technical contents of the present invention will be described in detail to enable the persons skilled in the art to easily understand the present invention.

It to be noted that the foregoing general description and the following detailed description are only intended to exemplify the present invention but not to limit the scope of the present invention.

DETAILED DESCRIPTION OF THE INVENTION

The present invention proposes a test strip with an identification function and a test instrument using the same, which applies to optical biotest, electrochemical biotest and immunological biotest, and which provides numerous identification signals to differentiate a lot of costumers, many types of test strips and many types of test instruments.

Figure 3:
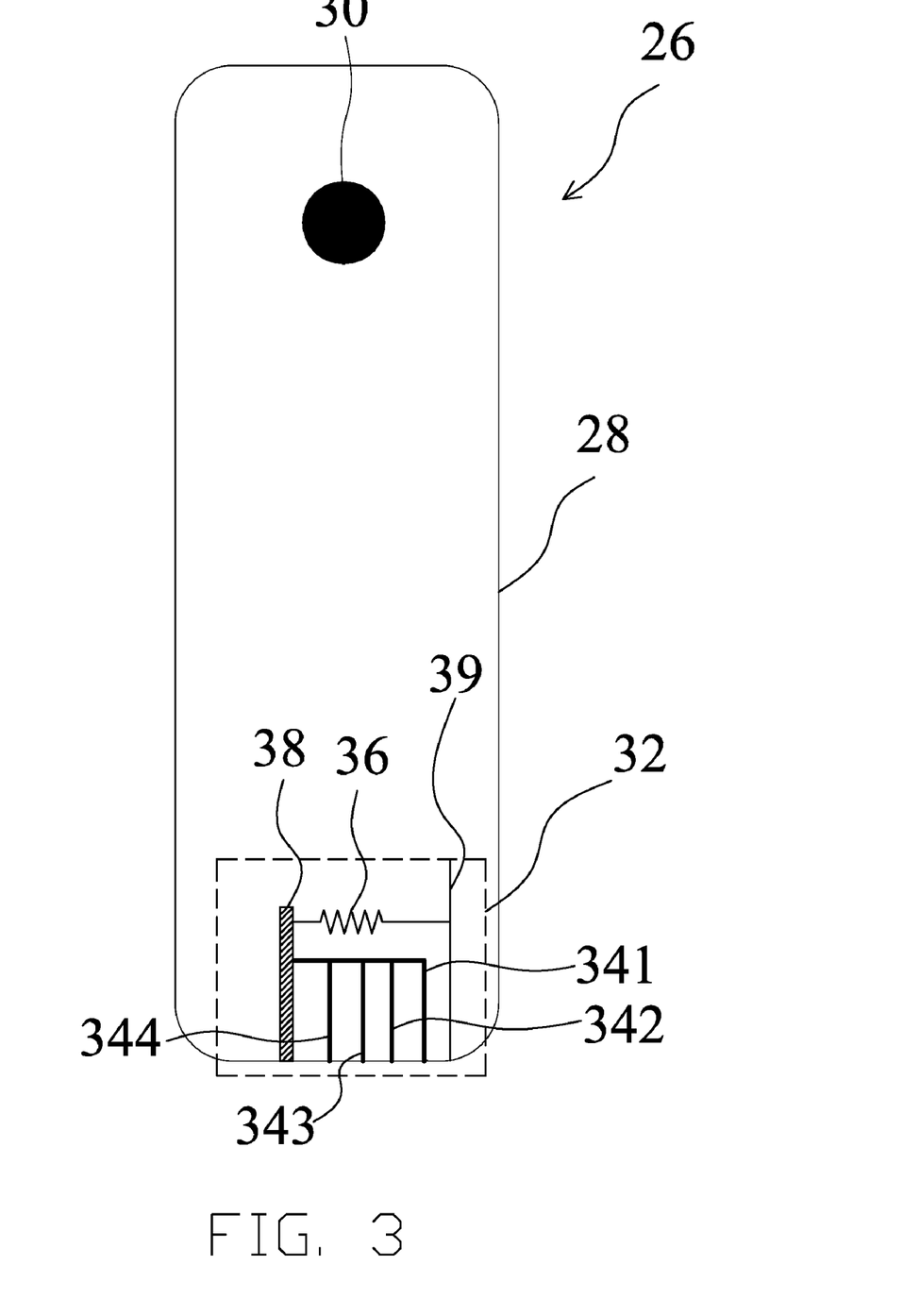
FIG. 3 is a diagram schematically showing the structure of a test strip according to a first embodiment of the present invention.

Refer to FIG. 3 a diagram schematically showing the structure of a test strip with an identification function according to a first embodiment of the present invention. The test strip in FIG. 3 is an optical test strip 26 comprising a substrate 28, an optical test area 30 on one end of the substrate 28 and an identification area 32 on the other end of the substrate 28. The identification area 32 has four identification electrodes 341-344, an electrode area and a resistor element 36. The four identification electrodes 341-344 generate digital identification signals. The electrode area has a ground electrode 38 and a power signal cable 39. The four identification electrodes 341-344 are all coupled to the ground electrode 38. The resistor element 36 is connected in parallel with the identification electrodes 341-344 and bridges over the ground electrode 38 and the power signal cable 39 to generate an analog identification signal. The digital and analog identification signals are used to carry the test code, analysis parameters, expiry date and/or batch number of a test strip. The identification electrodes 341-344 and resistor element 36 are preformed on the substrate 28 according to the required analysis parameters or other conditions; for example the resistance value of a printed resistance is selected according to the product type. The resistor element 36 is formed via coating on the substrate 28 a resistor paste having a resistance of between 20 ohm and 5M ohm, such as a metal, an alloy, a conductive ink, or a conductive paste (for example, TFR (Thick Film Resistor), a carbon paste, or a carbon paint). When the optical test strip 26 is inserted into a test instrument (not shown in the drawing), the identification area 32 is electrically coupled to the test instrument and generates digital identification signals. In the optical test strip 26, the connection states of the identification electrodes 341-344 and the resistances of the resistor element 36 can create a lot of identification signals.

Figure 4:
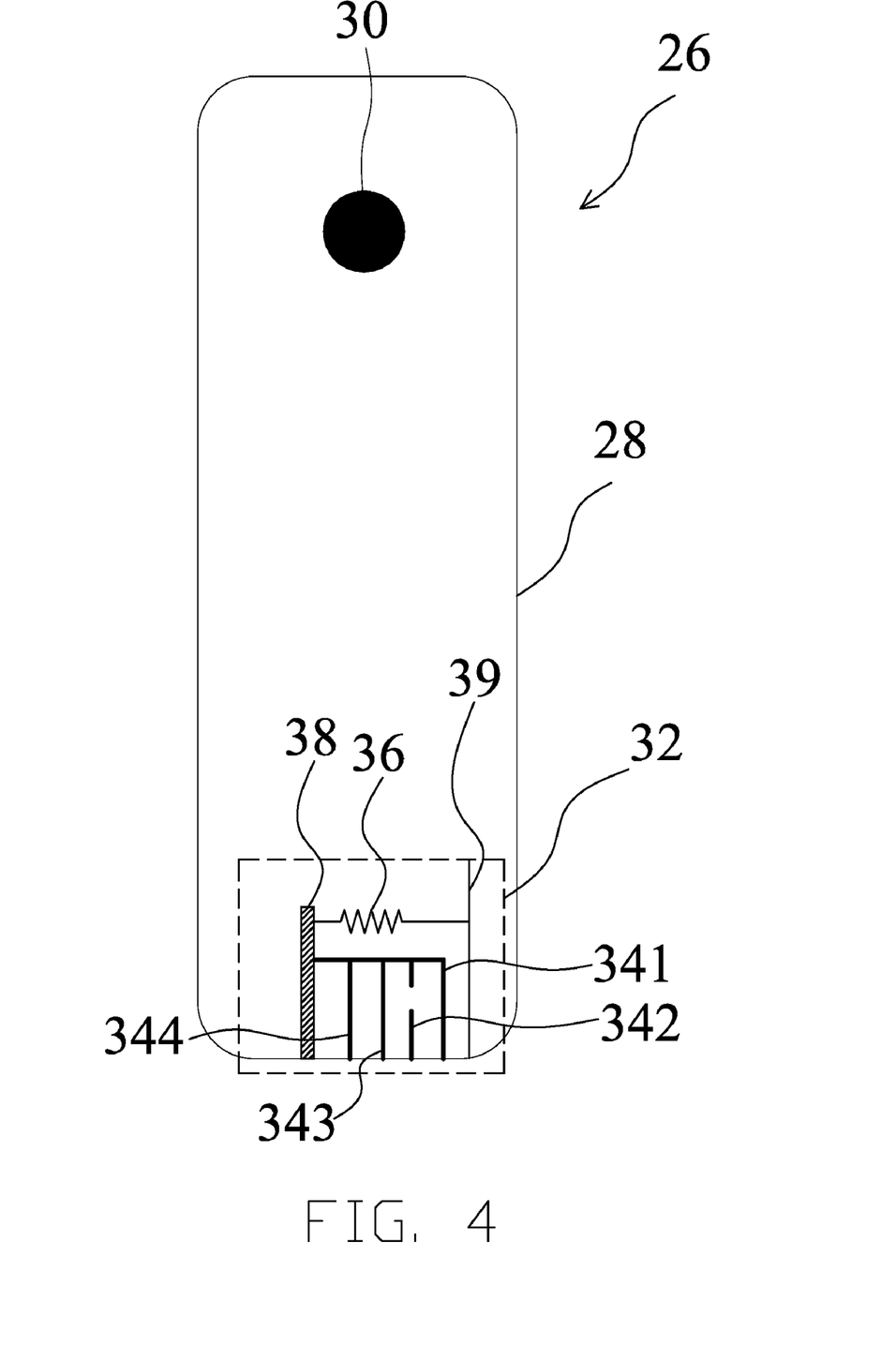
FIG. 4 is a diagram schematically showing another structure of the test strip according to the first embodiment of the present invention.

Refer to FIG. 4. After the fabrication and examination of a test strip is completed, at least one of the identification electrodes 341-344 is further fabricated into a open circuit structure with a punching method or a cutting method. Each of the identification electrodes 341-344 may be in a circuit-closed or circuit-opened, which can create a digital identification signal of "0" or "1". The four identification electrodes 341-344 can totally create $2^4$ sets of digital identification signals. The four identification electrodes 341-344 shown in FIG. 4 generate one set of digital identification signal (0, 1, 0, 0). If the resistor paste has m sets of resistances ranging from 20 to 5M ohm, there will be m sets of analog identification signals corresponding to the m sets of resistances. The combination of the m sets of analog identification signals and the $2^4$ sets of digital identification signals will generate $m \times 2^4$ sets of identification signals totally.

Figure 5:
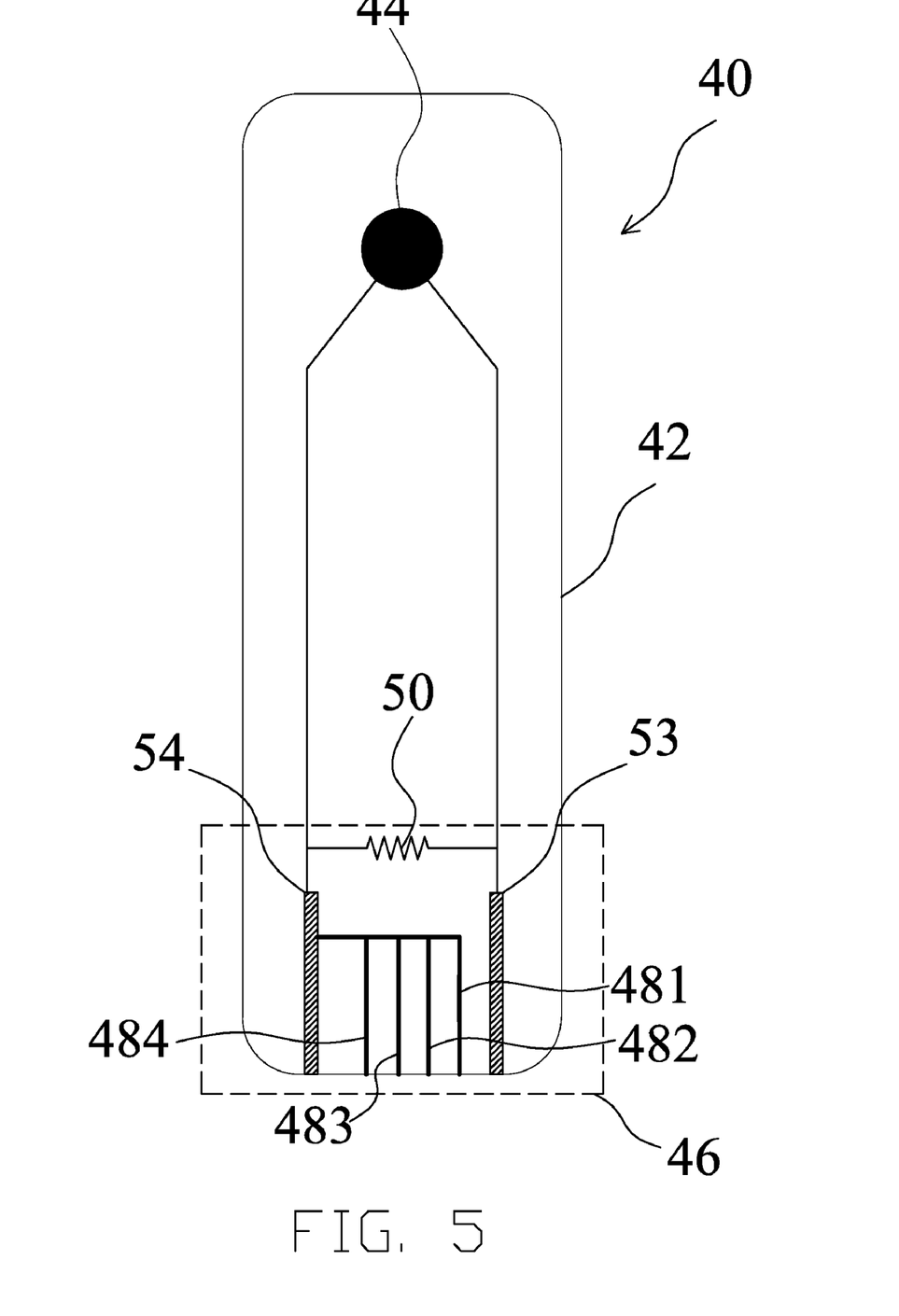
FIG. 5 is a diagram schematically showing the structure of a test strip according to a second embodiment of the present invention.

Refer to FIG. 5 a diagram schematically showing the structure of a test strip with an identification function according to a second embodiment of the present invention. The test strip in FIG. 5 is an electrochemical test strip 40 comprising a substrate 42, an electrochemical test area 44 on one end of the substrate 42 and an identification area 46 on the other end of the substrate 42. The identification area 46 has four identification electrodes 481-484, an electrode area and a resistor element 50. The four identification electrodes 481-484 generate digital identification signals. The electrode area is coupled to the electrochemical test area 44 and has a working electrode 53 and a counter electrode 54. The four identification electrodes 481-484 are all coupled to the counter electrode 54. The resistor element 50 is connected in parallel with the four identification electrodes 481-484 and bridges over the working electrode 53 and the counter electrode 54 to generate an analog identification signal. The digital and analog identification signals are used to carry the test code, analysis parameters, expiry date and/or batch number of a test strip. The identification electrodes 481-484 and resistor element 50 are preformed on the substrate 42 according to the required analysis parameters or other conditions; for example the resistance value of a printed resistance is selected according to the product type. The resistor element 50 is formed via coating on the substrate 62 a resistor paste having a resistance of between 20 ohm and 5M ohm, such as a metal, an alloy, a conductive ink, or a conductive paste (for example, TFR (Thick Film Resistor), a carbon paste, or a carbon paint). In the electrochemical test strip 40, the connection states of the identification electrodes 481-484 and the resistances of the resistor element 50 can create a lot of identification signals.

Figure 6:
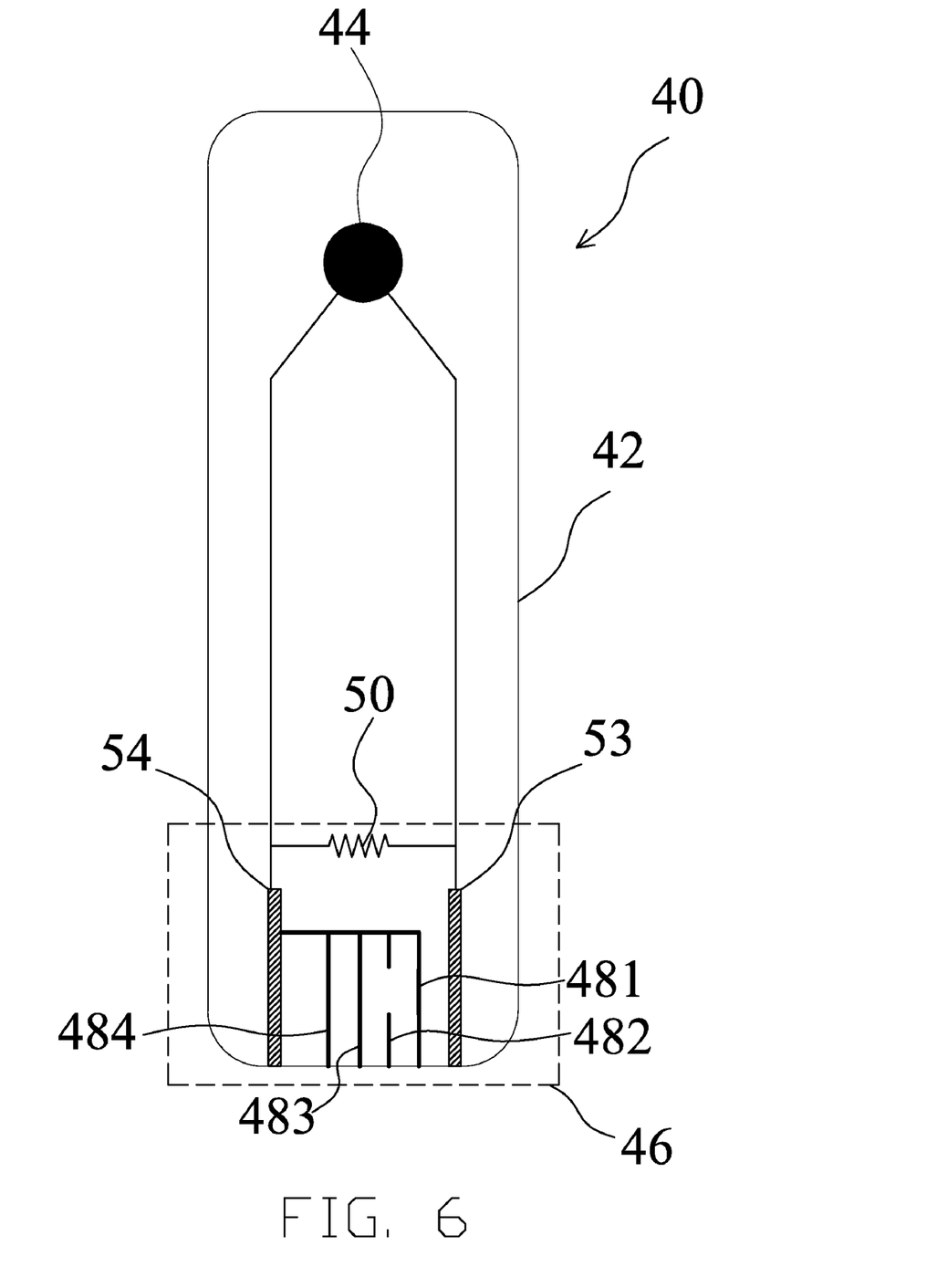
FIG. 6 is a diagram schematically showing another structure of the test strip according to the second embodiment of the present invention.

Refer to FIG. 6. After the fabrication and examination of a test strip is completed, at least one of the identification electrodes 481-484 of the electrochemical test strip 40 is further fabricated into an open circuit structure with a punching method or a cutting method. Thereby, the electrochemical test strip 40 can provide a lot of identification signals.

Figure 7:
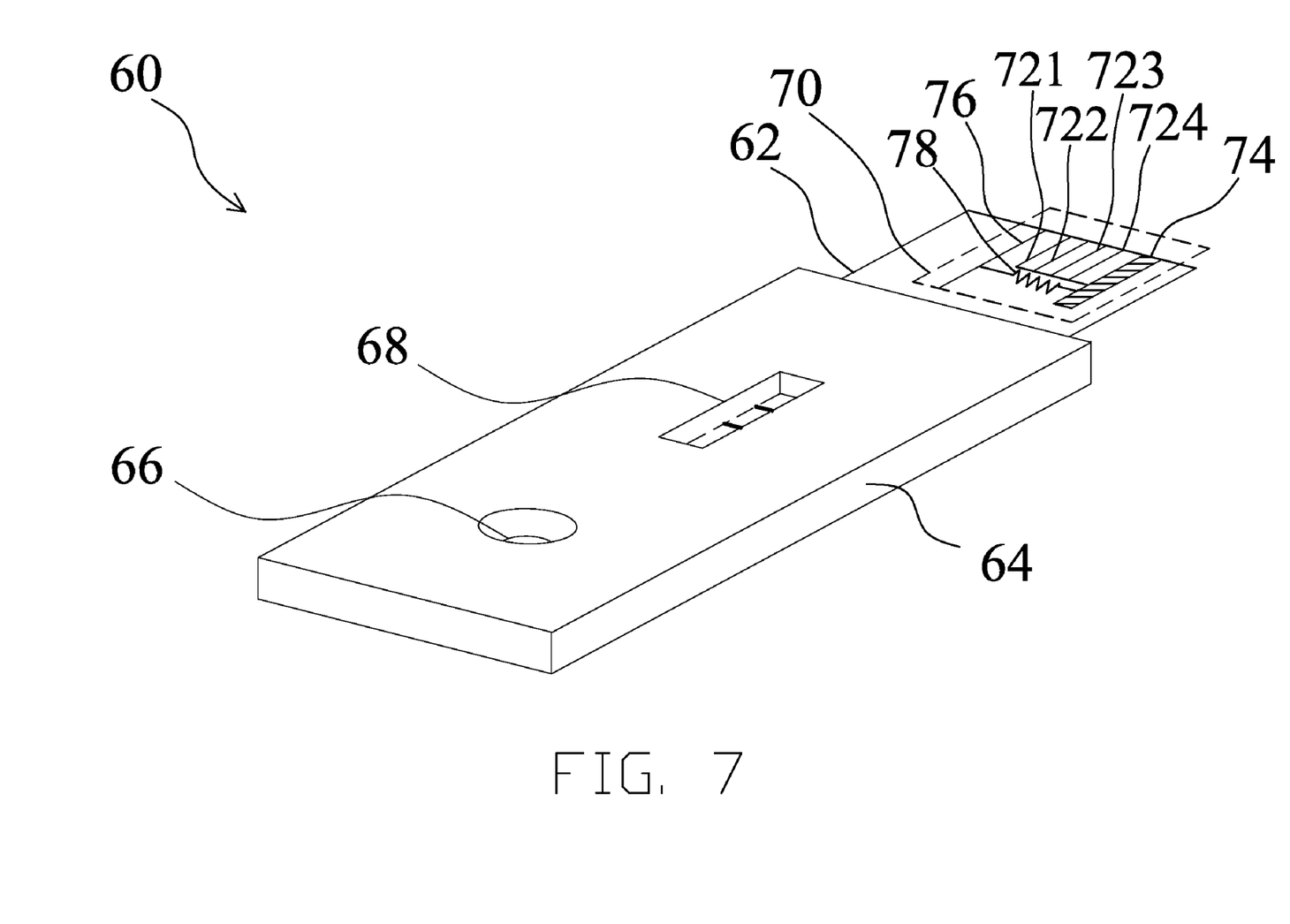
FIG. 7 is a diagram schematically showing the structure of a test strip according to a third embodiment of the present invention.

Refer to FIG. 7 a diagram schematically showing the structure of a test strip with an identification function according to a third embodiment of the present invention. The test strip in FIG. 7 is an immunological test strip 60 comprising a substrate 62, a suction area 66 on the substrate 62, a test area 68 also on the substrate 62, an identification area 70 also on the substrate 62, and a casing 64 encasing a portion of the substrate 62 and revealing the suction area 66, the test area 68 and the identification area 70. The test area 68 is a color reaction/colorimetric area. The identification area 70 has four identification electrodes 721-724, an electrode area and a resistor element 78. The four identification electrodes 721-724 generate digital identification signals. The electrode area has a ground electrode 74 and a power signal cable 76. The four identification electrodes 721-724 are all coupled to the ground electrode 74. The resistor element 78 is connected in parallel with the identification electrodes 721-724 and bridges over the ground electrode 74 and the power signal cable 76 to generate an analog identification signal. The digital and analog identification signals are used to carry the test code, analysis parameters, expiry date and/or batch number of a test strip. The identification electrodes 721-724 and the resistor element 78 are preformed on the substrate 62 according to the required analysis parameters or other conditions; for example the resistance value of a printed resistance is selected according to the production type. The resistor element 78 is formed via coating on the substrate 62 a resistor paste having a resistance of between 20 ohm and 5M ohm, such as a metal, an alloy, a conductive ink, or a conductive paste (for example, TFR (Thick Film Resistor), a carbon paste, or a carbon paint). In the immunological test strip 60, the connection states of the identification electrodes 721-724 and the resistances of the resistor element 78 can create a lot of identification signals.

Figure 8:
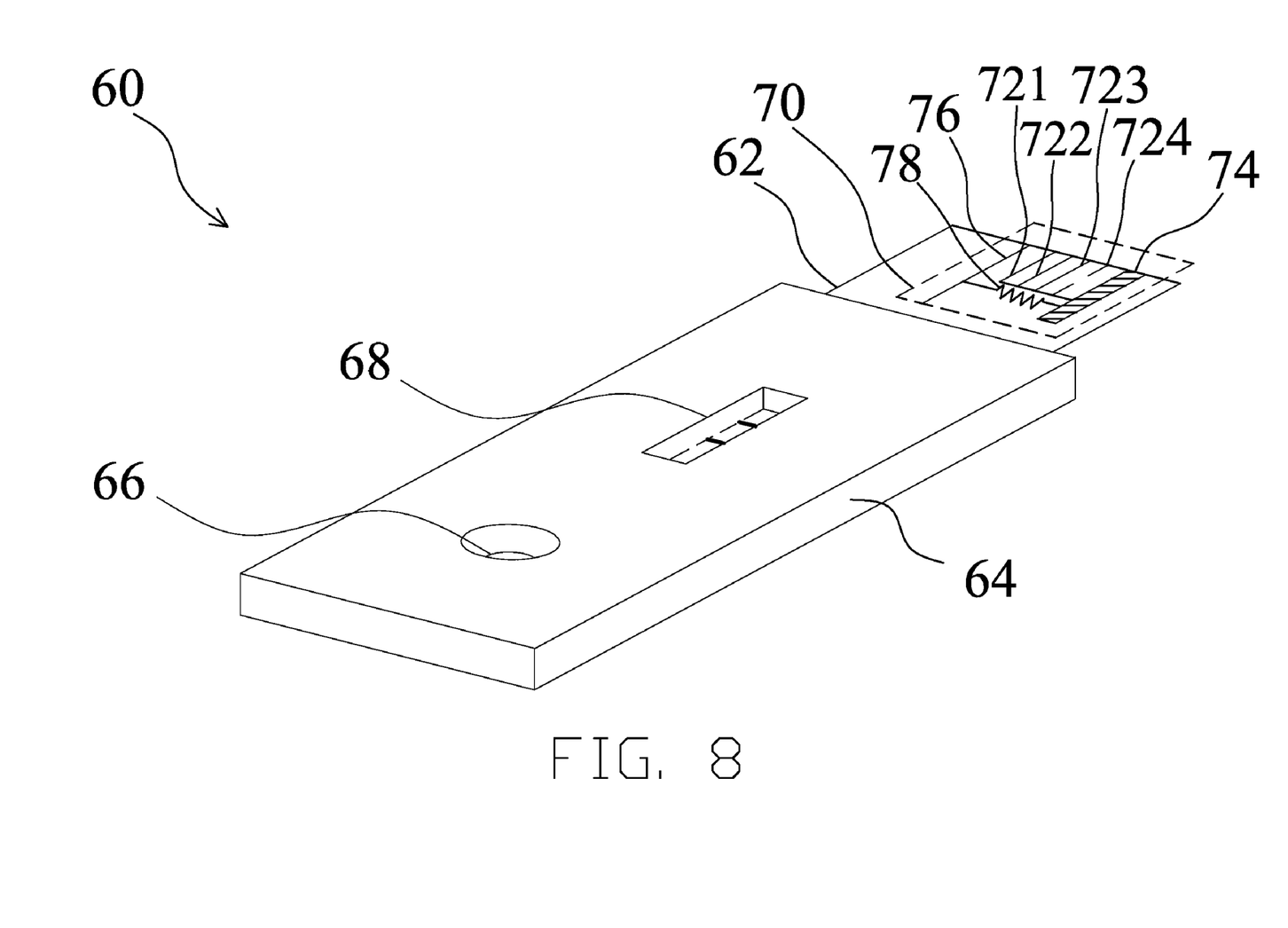
FIG. 8 is a diagram schematically showing another structure of the test strip according to the third embodiment of the present invention.

Refer to FIG. 8. After the fabrication and examination of a test strip is completed, at least one of the identification electrodes 721-724 of the immunological test strip 60 is further fabricated into an open circuit structure with a punching method or a cutting method. Thereby, the immunological test strip 60 can provide a lot of identification signals.

Figure 9:
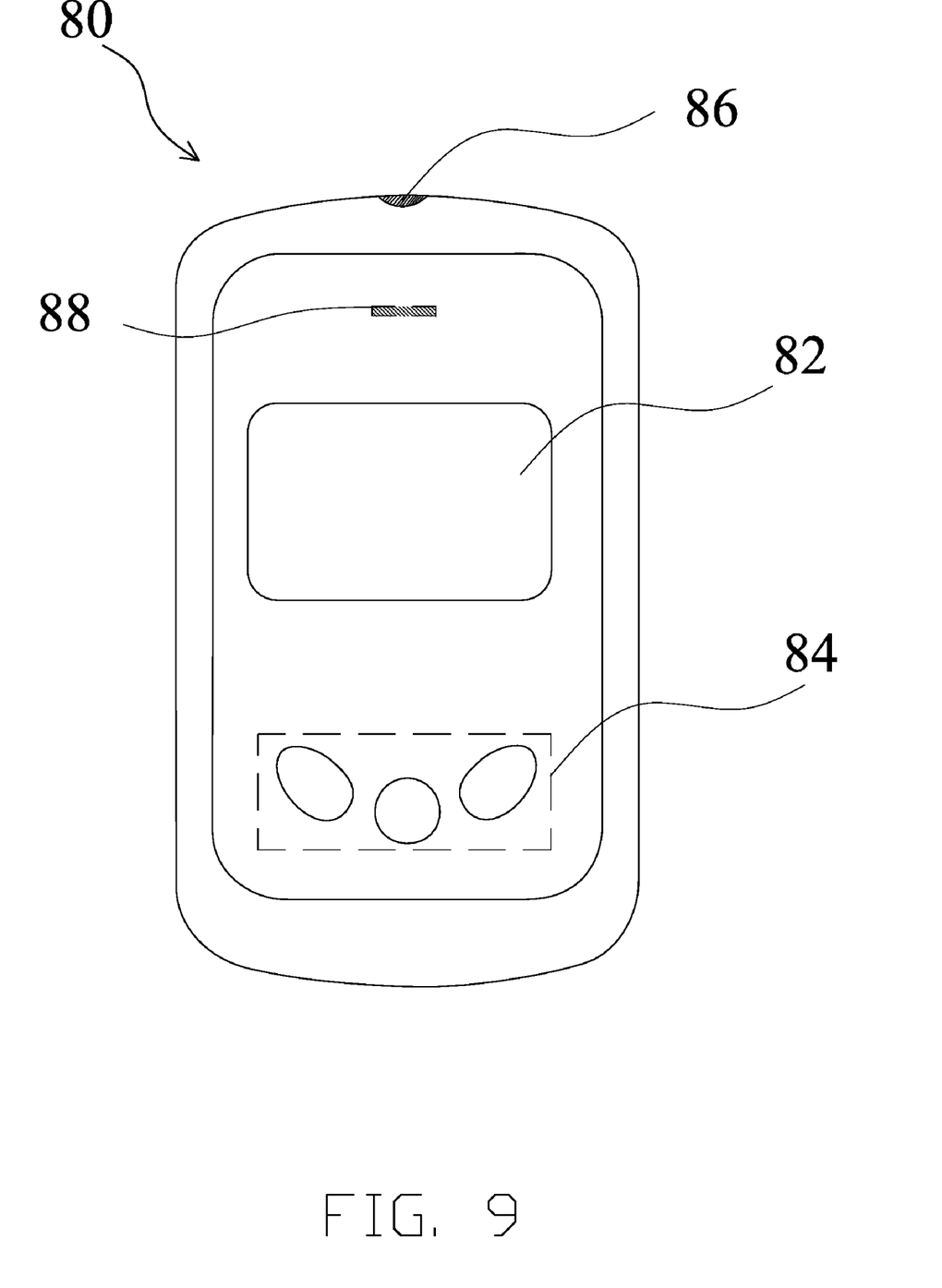
FIG. 9 is a diagram schematically showing a test instrument according to the present invention.

Refer to FIG. 9 a diagram schematically showing a test instrument according to the present invention. The test instrument 80 of the present invention comprises: a display 82, control buttons 84, a test port 86, and a detector 88. The test port 86 is an opening where a test strip is inserted. The detector 88 is arranged inside the test instrument and may be an electronic crosspoint connector. When the identification-area side of the test strip is inserted into the test port 86, the identification area is at a position corresponding to the detector 88. The detector 88 receives the digital identification signal of the identification electrodes and the analog identification signal of the resistor element and obtains the information of the test code, analysis parameters, expiry date, and/or batch number of the test strip. The test instrument also has a microprocessor (not shown in the drawings) used to analyze test data. As the microprocessor is not the feature of the present invention but a conventional device, the technical contents thereof will not be described herein.

The combinations of the identification electrodes and the resistor element of the present invention can provide many sets of identification signals to differentiate a lot of customers, many types of test strips and many types of test instruments. Therefore, the present invention can solve the problems of insufficient identification signals and unsatisfactory discrimination ability of the prior-art test strips. The present invention makes a user able to fast obtain a correct test results without inserting a code card into the test instrument or setting a test code and parameters for a test instrument.

The embodiments described above are to demonstrate the technical contents and characteristics of the present invention to enable the persons skilled in the art to understand, make, and use the present invention. However, it is not intended to limit the scope of the present invention. Therefore, any equivalent modification or variation according to the spirit of the present invention is to be also included within the scope of the present invention.

What is claimed is:

1. A test strip with an identification function comprising
   a substrate;
   a test area formed on said substrate;
   an identification area formed on said substrate and having
      N pieces of identification electrodes to generate a set of digital identification signal of "0" or "1" with N≧2, at least one resistor element connected in parallel with said identification electrodes to generate an analog identification signal, and an electrode area coupling said identification electrodes and said resistor element;
      said resistor element has m sets of resistance values to generate m sets of analog identification signals, and m≧1; and
      at least one of said N pieces of identification electrodes is fabricated into a open circuit structure; said N pieces of identification electrodes generate $2^N$ sets of digital identification signals, and said identification area generates m×$2^N$ sets of identification signals.

2. The test strip with an identification function according to claim 1, wherein said test area is an optical test area or an electrochemical test area.

3. The test strip with an identification function according to claim 2, wherein when said test area is an optical test area, said electrode area further comprises a ground electrode and a power signal cable; said ground electrode is coupled to said identification electrodes; said ground electrode and said power signal cable are coupled to said resistor element.

4. The test strip with an identification function according to claim 2, wherein when said test area is an electrochemical test area, said electrode area further comprises a working electrode and a counter electrode; said counter electrode is coupled to said identification electrodes; said working electrode and said counter electrode are coupled to said test area and said resistor element.

5. The test strip with an identification function according to claim 1, wherein at least one of said N pieces of identification electrodes is fabricated into an open circuit structure according to analysis parameters.

6. The test strip with an identification function according to claim 5, wherein at least one of said N pieces of identification electrodes is fabricated into an open circuit structure with a punching method or a cutting method.

7. The test strip with an identification function according to claim 1, wherein a combination of said digital signals and said analog signal represents a test code, analysis parameters, an expiry date, a batch number, a customer classification, a test instrument type, and/or a test strip type.

8. The test strip with an identification function according to claim 1, wherein said resistor element has a resistance value of between 20 ohm and 5M ohm.

9. The test strip with an identification function according to claim 1, wherein said resistor element is made of a resistor paste.

10. The test strip with an identification function according to claim 1 further comprising a casing encasing said substrate but revealing said test area and said identification area.

11. The test strip with an identification function according to claim 10, wherein said test area is color reaction/colorimetric area.

12. The test strip with an identification function according to claim 11, wherein said electrode area has a ground electrode and a power signal cable; said ground electrode is coupled to said identification electrodes; said ground electrode and said power signal cable are coupled to said resistor element.

13. A test instrument, cooperating with a test strip to perform a test, and comprising a test port and a detector arranged inside said test port, wherein an identification area of a test strip inserted into said test port is at a position corresponding to said detector; said detector generates an analog identification signal and a digital identification signal of "0" or "1" according to a resistor element and identification electrodes on said identification area; said test instrument receives said analog identification signal and said digital identification signal and obtains information of a test code, analysis parameters, an expiry data, a batch number, a customer classification, a test instrument type, and/or a test strip type of said test strip.

14. A test instrument according to claim 13, wherein said detector is an electronic crosspoint connector.

* * * * *